US007050166B2

(12) United States Patent
Bland et al.

(10) Patent No.: US 7,050,166 B2
(45) Date of Patent: May 23, 2006

(54) CALCIUM CARBONATE IMAGING TECHNIQUE

(75) Inventors: Ronald G. Bland, Houston, TX (US); Tom A. Jones, Cypress, TX (US)

(73) Assignee: Baker Hughes Incorporated, Houston, TX (US)

( * ) Notice: Subject to any disclaimer, the term of this patent is extended or adjusted under 35 U.S.C. 154(b) by 335 days.

(21) Appl. No.: 10/283,972

(22) Filed: Oct. 30, 2002

(65) Prior Publication Data

US 2003/0107735 A1 Jun. 12, 2003

Related U.S. Application Data

(60) Provisional application No. 60/338,311, filed on Nov. 2, 2001.

(51) Int. Cl.
*G01N 21/00* (2006.01)
*H04L 9/00* (2006.01)
*C09K 7/02* (2006.01)

(52) U.S. Cl. .................. 356/338; 356/441; 250/461.1; 507/112; 507/231; 424/405

(58) Field of Classification Search ........ 356/335–343, 356/73, 317; 250/461.1, 372, 573–575, 301, 250/255; 507/110–112, 212–231, 269; 424/405–406; 435/6, 91.1
See application file for complete search history.

(56) References Cited

U.S. PATENT DOCUMENTS

| | | | | |
|---|---|---|---|---|
| 3,662,605 A | * | 5/1972 | Grotyohann | 73/864.33 |
| 3,877,311 A | * | 4/1975 | Sugawara et al | 73/865.5 |
| 4,208,272 A | * | 6/1980 | Moudgil | 209/3.3 |
| 4,228,353 A | * | 10/1980 | Johnson | 250/356.1 |
| 4,229,653 A | * | 10/1980 | Uthe | 250/338.1 |
| 4,620,596 A | * | 11/1986 | Mondshine | 166/292 |
| 4,814,614 A | * | 3/1989 | Tsui | 250/301 |
| 5,055,694 A | * | 10/1991 | Jeffers et al. | 250/458.1 |
| 5,161,409 A | | 11/1992 | Hughes et al. | |
| 5,178,836 A | * | 1/1993 | Kitamori et al. | 422/73 |
| 5,211,677 A | * | 5/1993 | Sargeant et al. | 73/61.71 |
| 5,306,909 A | | 4/1994 | Jones et al. | |
| 5,316,983 A | * | 5/1994 | Fujimori et al. | 356/335 |
| 5,381,002 A | * | 1/1995 | Morrow et al. | 250/301 |
| 5,393,673 A | * | 2/1995 | Gjerde et al. | 436/171 |
| 5,415,228 A | * | 5/1995 | Price et al. | 166/278 |
| 5,428,451 A | | 6/1995 | Lea et al. | |
| 5,466,572 A | | 11/1995 | Sasaki et al. | |
| 5,469,251 A | * | 11/1995 | Kosaka et al. | 356/73 |
| 5,483,469 A | * | 1/1996 | Van den Engh et al | 702/21 |
| 5,504,062 A | | 4/1996 | Johnson | |
| 5,599,664 A | * | 2/1997 | Schwartz | 435/6 |
| 5,612,293 A | * | 3/1997 | Swartwout et al. | 507/110 |
| 5,627,143 A | * | 5/1997 | Sawdon | 507/103 |
| 5,633,503 A | | 5/1997 | Kosaka | |
| 5,644,388 A | | 7/1997 | Maekawa et al. | |
| 5,895,922 A | * | 4/1999 | Ho | 250/492.1 |
| 5,912,459 A | | 6/1999 | Mullins et al. | |
| 5,940,177 A | | 8/1999 | Esser et al. | |
| 6,027,740 A | * | 2/2000 | Puterka et al. | 424/405 |
| 6,100,222 A | * | 8/2000 | Vollmer et al. | 507/113 |
| 6,103,671 A | * | 8/2000 | Dobson et al. | 507/261 |
| 6,495,493 B1 | * | 12/2002 | Cobianco et al. | 507/110 |
| 6,525,325 B1 | * | 2/2003 | Andrews et al. | 250/461.1 |

FOREIGN PATENT DOCUMENTS

| | | |
|---|---|---|
| DE | 4405540 A1 | 8/1995 |
| EP | 0926482 A2 | 6/1999 |
| EP | 0926482 A3 | 6/1999 |
| JP | 04263388 A * | 9/1992 |

OTHER PUBLICATIONS

"What is Flow Cytometry?", Cancer Research UK [Internet]. [cited Jun. 5, 2002]: Available from; http://sci.cancerresearchuk.org/axp/facs/davies/Flow.html.
"What is Flow Cytometry?", Partec GmbH [Internet]. 2002 [cited Jun. 5, 2002]: Available from: www.partec.de/partec/flowcytometry.html.
PCT International Search Report for International Application No. PCT/US02/34998, Mar. 21, 2003.

* cited by examiner

*Primary Examiner*—Gregory J. Toatley, Jr.
*Assistant Examiner*—Sang H. Nguyen
(74) *Attorney, Agent, or Firm*—Madan, Mossman & Sriram, P.C.

(57) ABSTRACT

The invention concerns a method for determining the particle size distribution (PSD) of bridging agents in fluids, particularly aqueous fluids used in hydrocarbon recovery such as drilling fluids, drill-in fluids, completion fluids, and the like. It was discovered that the PSD could be selectively determined for calcium carbonate as a bridging agent because it auto-fluoresces. The method is reproducible and is not bothered by the presence of other particles such as drill solids which interferes with conventional methods, for instance, light-scattering techniques. The light used to fluoresce the bridging agent may be filtered to a particular frequency if there are other components present that fluoresce. Flow cytometry is another technique that could be used to implement the invention.

22 Claims, No Drawings

CALCIUM CARBONATE IMAGING TECHNIQUE

CROSS-REFERENCE TO RELATED APPLICATION

This application claims the benefit of U.S. provisional application No. 60/338,311 filed Nov. 2, 2001.

FIELD OF THE INVENTION

The present invention relates to methods for determining the presence and proportion of certain additives in fluids, and more particularly relates, in one embodiment, to methods for determining the presence and proportion of bridging agents in aqueous drilling fluids, drill-in fluids and completion fluids.

BACKGROUND OF THE INVENTION

Drilling fluids used in the drilling of subterranean oil and gas wells as well as other drilling fluid applications and drilling procedures are known. In rotary drilling there are a variety of functions and characteristics that are expected of drilling fluids, also known as drilling muds, or simply "muds". The drilling fluid is expected to carry cuttings up from beneath the bit, transport them up the annulus, and allow their separation at the surface while at the same time the rotary bit is cooled and cleaned. A drilling mud is also intended to reduce friction between the drill string and the sides of the hole while maintaining the stability of uncased sections of the borehole. The drilling fluid is formulated to prevent unwanted influxes of drilling fluid filtrate and drill solids into permeable rocks penetrated and also often to form a thin, low permeability filter cake which temporarily seals pores, other openings and formations penetrated by the bit. The drilling fluid may also be used to collect and interpret information available from drill cuttings, cores and electrical logs. It will be appreciated that within the scope of the claimed invention herein, the term "drilling fluid" also encompasses "drill-in fluids" and "completion fluids".

Drilling fluids are typically classified according to their base fluid. In water-based muds, solid particles are suspended in water or brine. Oil can be emulsified in the water. Nonetheless, the water is the continuous phase. Oil-based muds are the opposite or inverse. Solid particles are suspended in oil, and water or brine is emulsified in the oil and therefore the oil is the continuous phase. Oil-based muds that are water-in-oil emulsions are also called invert emulsions. Brine-based drilling fluids, of course are a water-based mud in which the aqueous component is brine.

Horizontal wells drilled and completed in unconsolidated sand reservoirs have become feasible due to improvements in technology and completion methods. Wells of this type require sand control, for example such as long open hole gravel packs or the installation of mechanical sand exclusion devices (slotted liners, pre-packed and expandable sand screens, etc.). Successful wells have been completed with horizontal, producing intervals as long as 5,000 ft. (1224 m) using these methods of sand control.

Usually the wells are drilled with conventional drilling muds to the top of the pay zone and the casing is set. The cement is then drilled out to the casing shoe and the shoe is tested. The drilling mud is then displaced with a "low damage potential drilling mud" generally consisting of polymers or other thickening agents, viscosity enhancers and insoluble particles for building a filter cake to bridge the pores in the sandstone reservoir. The particles are usually graded salt (NaCl) in saturated brine or graded calcium carbonate ($CaCO_3$) in any fluid, and as technology has improved, the particle size distribution as compared with the pore throat openings of the reservoir has become more important. Sodium chloride and calcium carbonate are used because they are soluble in undersaturated brines or inorganic and/or organic acids, respectively.

Matching the particle size distribution (PSD) of bridging agents in drill-in fluids to the pore size openings of sandstone reservoirs being drilled is important for achieving spurt loss control and minimizing permeability reduction in the reservoir from undesirable fluid and particulate invasion. This matching is fairly straightforward in preparing the initial drill-in fluid and can be verified by, for example, laser light scattering prior to drilling since the bridging agent is typically the only particulate solid present. Once drilling begins, however, the drill-in fluid becomes contaminated with drill solids (cuttings) and other particulate components such as weighting agents and laser light scattering will only give the PSD of all the suspended solids—drill solids, weighting agents, and the bridging agent. It is important to distinguish between the solids to determine what percentage of the solids in any size range are capable of actually being removed from the pore throats of the formation by undersaturated brine or acid after drilling. It is also important to determine what size of bridging particle should be added to the drilling fluid to make up for what is consumed or degraded in the drilling process.

It would be desirable if methods could be devised to determine how much of a bridging agent only is present in a fluid, such as in a recirculated drilling mud, as distinct from other solids that may be present.

SUMMARY OF THE INVENTION

Accordingly, it is an object of the present invention to provide a method to determine the presence and/or a characteristic of a bridging agent, particularly calcium carbonate, in a fluid used for hydrocarbon recovery, such as a drilling fluid, drill-in fluid, and/or completion fluid, and the like.

It is another object of the present invention to provide a method to determine the PSD of calcium carbonate in a fluid used in hydrocarbon recovery.

Still another object of the invention is to provide a method for determining the PSD of a bridging agent, such as calcium carbonate, in a drilling fluid used for hydrocarbon recovery, even in the presence of other particulate solids, such as drill cuttings and weighting agents.

In carrying out these and other objects of the invention, there is provided, in one form, a method for determining a characteristic of a particulate material in a fluid involving exposing a sample of the fluid containing the particulate material to light, observing the fluorescence of the particulate material to produce an image; and calculating a characteristic of the particulate material using the image. The particulate material characteristic may be the size of the bridging agent, the amount of the particulate material, or the combination of size and amount of the particulate material expressed as particle size distribution (PSD). The invention can also be applied to measuring the characteristics (amount, size or both) of an auto-fluorescing particulate in a fluid and especially if that particulate is used as a bridging agent.

In another embodiment of the invention, there is provided, in another form, a method for determining a characteristic of an immiscible phase in a fluid that involves exposing a sample of the fluid containing the immiscible phase to light;

observing the fluorescence of the immiscible phase to produce an image; and calculating a characteristic of the immiscible phase using the image. Again, the characteristic may be the size of the immiscible phase, the amount of the immiscible phase and a combination of size and amount of the immiscible phase. The immiscible phase is either an auto-fluorescing immiscible phase or an immiscible phase to which a fluorescent dye has been added.

DETAILED DESCRIPTION OF THE INVENTION

Because many additives for aqueous fluids (such as those used in hydrocarbon recovery) are relatively expensive, it is desirable to only use as much additive as is necessary to achieve the desired purpose. Time and logistics constraints for even inexpensive additives, where several varieties are available, may make it imperative that only the most efficient varieties are used. However, it is also necessary to determine that enough additive is present to achieve the purpose for which it is used, and/or to determine that the additive is still effective. These considerations are true for bridging agents as well. With respect to bridging agents, it is important to know when to add how much of the proper size of bridging agent, and thus knowing the particle size distribution (PSD) of the bridging agent in the return drilling mud is important. The method of this invention is expected to be useful in determining the presence, size and/or amount of any immiscible phase in a fluid, where an immiscible phase includes additives and particulate materials (e.g. bridging agents) and any other material in a fluid which is insoluble therein whose presence, size and/or amount can be determined by the instant method. For instance, the method of this invention could be used to determine the size and/or amount of proppant in a fracturing fluid, the size and/or amount of specially sized calcium carbonate in a reservoir drill-in fluid or loss of circulation pill containing sized calcium carbonate.

The term "proportion" as used herein can refer to the amount of the immiscible phase as well as distribution, which is a combination of size and amount. When a fluid is described as "aqueous", it is meant that it contains at least some water, and in a preferred, non-limiting embodiment, contains at least 50 volume % water, and in another preferred, non-limiting embodiment contains water as the continuous phase, whether or not water makes up 50 vol. % of the total fluid.

It is expected that the technique of this invention would be useful in determining characteristics of a bridging agent or other auto-fluorescing particulate within a mixture of particulates, such as a powder, as well as in a fluid. As will be explained, the method of this invention can be modified or adapted for non-fluorescing particles by incorporation of a suitable dye.

It has been discovered that certain bridging agents, in particular calcium carbonate, have a relatively high level of auto-fluorescence. This high level of auto-fluorescence of calcium carbonate can be used to obtain an image of the calcium carbonate distinguishable from the remaining drill solids and weight material that exhibit relatively lower levels of auto-fluorescence. It will be appreciated that the term "image" as defined herein is not limited to any particular medium, and includes, but is not necessarily limited to, images in fixed form such as photographs, images on a screen (cathode ray tube, flat panel display, images perceivable by charge-coupled devices (CCDs), etc. of a temporary nature), images in machine-readable form, etc. Such images may be captured using a microscope having fluorescence imaging capability or other collection objects or electronics. The resulting images of just calcium carbonate can then be analyzed using commercial image analysis software programs to calculate the PSD of only the calcium carbonate bridging agents present in field drill-in fluids (or other fluids) contaminated with drill solids. The inventive method is particularly useful in analyzing selectively for calcium carbonate. Conventional light-scattering analysis is sensitive to all particles and does not differentiate between bridging agents and drill solids.

The inventive technique can also be used to trace calcium carbonate particulate invasion of laboratory or field cores after mudding off or coring. If field cores were available on location, the Technical Service Representative (TSR) could test the treated fluid to determine if the bridging agent was performing appropriately on the cores, i.e. if the agent was properly bridging and minimizing invasion as measured by spurt and total filtration losses. Alternatively, simulated cores could be used. The advantage of analyzing this at the drilling location is that appropriate adjustments to the drilling fluids' PSD could be adjusted in a timely manner to avoid potential formation damage caused by fluid and particulate invasion.

With the imaging technique of the invention, it is assumed that the pore throat size distribution of the formation is already known (such as from a previously drilled offset well) or can be estimated. As drilling into the reservoir began, the TSR could check and adjust the PSD as needed based on the fluorescence data and the known pore size distribution.

While dyes can be used as tracers for immiscible phases, it is particularly advantageous when a fluorescent dye does not have to be used, that is, when the particle of interest auto-fluoresces, since it simplifies the process. Calcium carbonate is presently the only known bridging agent that auto-fluoresces, but an exhaustive study has not been done of all bridging agents, so it is possible that there are others with this property. It is not known why calcium carbonate auto-fluoresces. One non-limiting theory that the inventors do not necessarily wish to be bound by is that the fluorescent property is organic in origin, that is, that it is due to organic material laid down when the calcium carbonate was formed. However, it is not necessary to explain why calcium carbonate auto-fluoresces to exploit the property.

In some drilling fluid systems, there may be other species present that fluoresce and adjustments may need to be made in the inventive process. Other components, such as an emulsifier or other material may fluoresce at a frequency that might interfere with that of the bridging agent. It may be possible to use a filter to isolate the fluorescence of interest or reduce the intensity of the interfering fluorescence. A filter could be used on the light used to expose the sample, to filter he fluorescing light, or both. Alternatively, the light source itself could be of a particular narrow frequency. In addition, or in the alternative, the detector or observation and/or the image produced in the observation of the illuminated immiscible phase could be modified to be sensitive only to a particular, desired wavelength of interest. All of these methods would be expected to be useful in modifying the light used to observe the fluorescence of the bridging agent or particulate. Of course, observing the fluorescence of the bridging agent or other immiscible phase means being able to detect the presence, size and/or amount of the immiscible phase from other light that may be present.

Separate fluorescent dyes could also be used as tracers in the continuous phase of a drilling fluid, as well as to track filtrate invasion in cores, whether field cores or simulated cores. In some alternate embodiments of the invention, a dye could be added to the sample of the fluid (drill-in fluid, e.g.) after the fluid is retrieved from the borehole. By "fluorescent dye" is meant any substance that would selectively bind to an immiscible phase or to the continuous phase and preferentially be detectable under observation and/or image production to show the presence of the immiscible phase or the continuous phase, by using either a broad or a narrow wavelength spectrum of light, as necessary or preferable. If a fluorescent dye is used in both the continuous and the immiscible phases, a different dye would generally be used for each phase, and a different species and/or phase would be examined using each dye. These separately added dyes could be used separately from or in addition to auto-fluorescing particles or agents.

Such challenges would have to be addressed on a case-by-case basis and generalizations cannot be made. Because these drilling fluid systems are complex, it would be impossible to predict in advance whether or not the inventive approach would work smoothly the first time on a particular system since the fluorescence of the components, and of the various species that would also be present in the recirculated mud from the formation are not characteristics that are generally known in advance. In some cases, if the other particulate or species that auto-fluoresces does so at substantially less intensity than the bridging agent being analyzed for, then corrective measures such as filtering or changing the light source may not be necessary. It is expected that in some cases changes in the fluorescent microscope settings and/or the analysis software could sufficiently eliminate any interference from other species to obtain meaningful data for the bridging agent.

In one non-limiting embodiment of this invention, flow cytometry technology may be used to implement the inventive method. Flow cytometry is a method of measuring certain physical and/or chemical characteristics of particles as they travel in a fluid, such as a suspension or a dilute solution of a dispersion, individually past a sensing point, usually an optical detector. The technique can be used to count or measure the characteristics of cells. Flow cytometers can be understood to be specialized fluorescence microscopes. Flow cytometers include a light source, collection optics, electronics and a computer to translate signals into usable data. Many commercial cytometers use a laser as the light source that emits coherent light at a specified wavelength although broadband light sources can also be used. Scattered and emitted fluorescent light is typically collected by two lenses (one set in front of the light source and one set at right angles thereto) and by a series of optics, beam splitters and filters, specific bands of fluorescence can be measured. Physical characteristics such as particle size and shape can be determined, and any function that can be detected by a fluorescent compound can be examined. Many flow cytometers also have the ability to sort or physically separate particles of interest from a sample. An important feature of flow cytometric analysis is that large numbers of particles, for instance on the order of 100,000 or more may be analyzed one after the other in a relatively short period of time (e.g. one minute). In contrast, microscopic analysis is usually based on a limited number of particles (e.g. 1 to 100) seen on a slide.

The invention will be illustrated further with reference to the following Example that is not intended to limit the invention, but to give an idea of how the invention might be implemented.

EXAMPLE 1

The analysis process of the invention would involve first taking a smear of the whole mud or diluted whole mud on a microscope slide. A field or area of the slide would be photographed using fluorescent illumination. Additionally images may also be taken using bright-field transmitted light, reflected light and/or dark-field illumination all with or without polarization. These images would then be analyzed using an image analysis software program to identify the particle boundaries, determine their diameters, and count the particles. Commercial programs available to do this type of analysis include, but are not limited to IMAGEPRO and OPTIMUS software marketed by Media Cybernetics, but mention of these programs should not be understood as an endorsement of any kind. Several fields should be used to get a good statistical average of the range of particle diameters. Preferably, this process would be repeated at a range of magnifications to ensure that the full range of sizes was captured. A histogram of the particle counts versus particle size range would then give the relative PSD for each type of illumination. If the volume of the sample counted was actually determined, then an absolute PSD could be obtained. Comparison of results using different illumination would be used to discriminate particle types. In another embodiment of the invention, flow cytometry could be employed to count particles in a given volume of a flowing stream as they pass a sensing point.

The inventive analysis could be done at the rig site in a mobile laboratory, or even in the mud logger's cabin provided it was equipped with a fluorescent microscope with the imaging capability and analysis software. Alternatively, the image(s) obtained at the rig site could be electronically transmitted, such as by e-mail or possibly fax, to another location for analysis. It is anticipated that this is the only equipment needed to practice the method of the invention in its basic form, in one non-limiting embodiment.

In the foregoing specification, the invention has been described with reference to specific embodiments thereof, and has been proposed as effective in providing a reproducible method for determining the size, amount, and/or PSD of bridging agents in fluid systems, such as drilling fluids, drill-in fluids, and completion fluids. Additionally, the method of this invention is expected to be useful in determining the presence, amount, size, and PSD of any auto-fluorescing particulate in other fluids as well, with the expected modifications. Further, it will be evident that various modifications and changes can be made to the inventive method without departing from the broader spirit or scope of the invention as set forth in the appended claims. Accordingly, the specification is to be regarded in an illustrative rather than a restrictive sense. For example, specific systems of bridging agents, fluid systems and other common drilling system additives, falling within the claimed parameters, but not specifically identified or tried in a particular method, are anticipated to be within the scope of this invention. Similarly, routine modifications of the inventive test method, such as by using fluorescent light or filters of different frequencies or using different test equipment would be expected to fall within the scope of the invention. Also, known counting technologies such as flow cytometry, or future counting technologies, would be expected to be useful in performing the inventive method.

We claim:

1. A method for determining a characteristic of a particulate material in a fluid comprising:
   (a) exposing a sample of the fluid containing the particulate material to light:
   (b) observing the fluorescence of the particulate material to produce an image; and
   (c) calculating a characteristic of the particulate material using the image, where the characteristic is selected from the group consisting of:
      (I) the size of the particulate material
      (ii) the amount of the particulate material; and
      (iii) a combination of size and amount of the particulate material expressed as a particle size distribution (PSO),
   in the absence of laser light scattering, and where the fluid contains particles other than the particulate material.

2. The method of claim 1 where the particulate material auto-fluoresces.

3. The method of claim 1 where the particulate material is calcium carbonate.

4. The method of claim 1 in the absence of adding fluorescent dye to the particulate material agent.

5. The method of claim 1 further comprising modifying the light used in the observing to observe the fluorescence of the particulate material.

6. The method of claim 1 where the material is not calcium carbonate, and a fluorescent dye is added to the particulate material prior to its insertion into the fluid.

7. The method of claim 1 where the fluid is an aqueous fluid used for hydrocarbon recovery and is selected from the group consisting of drilling fluids, drill-in fluids, and completion fluids.

8. The method of claim 1 where (a) and (b) are performed with a flow cytometer.

9. The method of claim 1 where the particulate material is a bridging agent.

10. A method for determining a characteristic of an immiscible phase in a fluid comprising:
    (a) exposing a sample of the fluid containing the immiscible phase to light;
    (b) observing the fluorescence of the immiscible phase to produce an image; and
    (c) calculating a characteristic of the immiscible phase using the image, where the characteristic is selected from the group consisting of:
       (i) the size of the immiscible phase;
       (ii) the amount of the immiscible phase; and
       (iii) a combination of size and amount of the immiscible phase;
    where the immiscible phase is selected from the group consisting of auto-fluorescing immiscible phases and immiscible phases to which a fluorescent dye has been added, and in the absence of laser light scattering.

11. The method of claim 10 where the immiscible phase is calcium carbonate and where the fluid is an aqueous fluid used for hydrocarbon recovery and is selected from the group consisting of drilling fluids, drill-in fluids, and completion fluids.

12. The method of claim 10 where the fluid contains particles other than the immiscible phase.

13. The method of claim 10 further comprising modifying the light used in the observing to observe the fluorescence of the immiscible phase.

14. The method of claim 10 where (a) and (b) are performed with a flow cytometer.

15. A method for determining a particle size distribution (PSD) of a bridging agent in a fluid comprising:
    exposing a sample of the fluid containing the bridging agent to light, where the fluid is selected from the group consisting of drilling fluids, drill-in fluids, and completion fluids;
    observing the fluorescence of the bridging agent to produce an image; and
    calculating the PSD of the bridging agent using the image, in the absence of laser light scattering, and where the fluid contains particles other than the bridging agent.

16. The method of claim 15 where the bridging agent auto-fluoresces.

17. The method of claim 15 where the bridging agent is calcium carbonate.

18. The method of claim 15 in the absence of adding fluorescent dye to the bridging agent.

19. The method of claim 15 further comprising modifying the light used in the observing to observe the fluorescence of the bridging agent.

20. The method of claim 15 where exposing the sample and observing the fluorescence are performed with a flow cytometer.

21. A method for determining a characteristic of a particulate material in a fluid comprising:
    (a) exposing a sample of the fluid containing the particulate material to light;
    (b) observing the fluorescence of the particulate material to produce an image; and
    (c) calculating a characteristic of the particulate material using the image, where the characteristic is selected from the group consisting of:
       (i) the size of the particulate material
       (ii) the amount of the particulate material; and
       (iii) a combination of size and amount of the particulate material expressed as a particle size distribution (PSD),
    in the absence of laser light scattering, and where the fluid is used for hydrocarbon recovery and is selected from the group consisting of drilling fluids, drill-in fluids, and completion fluids, and where the fluid contains particles other than the particulate material.

22. A method for determining a characteristic of a particulate material in a fluid comprising:
    (a) exposing a sample of the fluid containing the particulate material to light;
    (b) observing the fluorescence of the particulate material to produce an image; and
    (c) calculating a characteristic of the particulate material using the image, where the characteristic is selected from the group consisting of:
       (i) the size of the particulate material
       (ii) the amount of the particulate material; and
       (iii) a combination of size and amount of the particulate material expressed as a particle size distribution (PSD),
    in the absence of laser light scattering, where (a) and (b) are performed with a flow cytometer, and where the fluid contains particles other than the particulate material.

* * * * *